(12) United States Patent
Martin et al.

(10) Patent No.: US 7,028,557 B2
(45) Date of Patent: Apr. 18, 2006

(54) METHOD AND PROCEDURE TO MEASURE FLUID FLOW AND FLUID FRACTION, AND EQUIPMENT USED TO THAT END

(75) Inventors: Carlos Alberto Martin, Córdoba (AR); Daniel José Pusiol, Córdoba (AR); Máximo Elias Ramia, Córdoba (AR); Jorge Miguel Garnero, Córdoba (AR); Eduardo David Fried, Córdoba (AR)

(73) Assignee: Back Office Service Solutions S.R.L., Cordoba (AR)

( * ) Notice: Subject to any disclaimer, the term of this patent is extended or adjusted under 35 U.S.C. 154(b) by 106 days.

(21) Appl. No.: 10/270,178

(22) Filed: Oct. 11, 2002

(65) Prior Publication Data
US 2004/0015332 A1 Jan. 22, 2004

(30) Foreign Application Priority Data
Oct. 12, 2001 (AR) .................................. P010104816

(51) Int. Cl.
*G01P 5/08* (2006.01)

(52) U.S. Cl. ....................................... 73/861.08

(58) Field of Classification Search ............. 73/861.08, 73/152.08, 152.14, 152.16, 152.18, 152.21, 73/861.18; 324/303, 306
See application file for complete search history.

*Primary Examiner*—Edward Lefkowitz
*Assistant Examiner*—Corey D. Mack
(74) *Attorney, Agent, or Firm*—Thorpe North & Western (57) ABSTRACT

A procedure for determination of flow and fraction of fluids includes the steps of: determination of Spin-Lattice relaxation times to be measured; assignment of radiofrequency pulse sequences corresponding to each of the fluids to be measured and with the fluid flow; application of a radiofrequency pulse sequence to a first coil; application of a second radiofrequency pulse sequence to the first coil; and application of a third radiofrequency pulse sequence to a second coil.

15 Claims, 10 Drawing Sheets

METHOD AND PROCEDURE TO MEASURE FLUID FLOW AND FLUID FRACTION, AND EQUIPMENT USED TO THAT END

RELATED APPLICATIONS

This application claims priority to Argentina Patent Application No. P010104816, filed Oct. 12, 2001.

BACKGROUND OF THE INVENTION

The identification of the fluids conveyed in a duct, as well as measurements of the fluid flow and fluid fractions of mixed fluids are needed in a large number of industrial processes or applications. For example, in the cases of the extractive oil industry and the petrochemicalindustry, it is important to know, at any given time, the quantities of oil, water and gas flowingthrough a duct coming from an oil well. In addition, it is important to be able to identify given effluents, such pollutants, in process industries, such as the food industries, etc. This is the case in the oil industry, since the obtained data allows quantifying primary well production, as well as the success achieved with secondary extraction. In these wells high pressure fluid injection is used for recovery of remaining oil.

In order to carry on the above-mentioned measurements, sampling procedures are used in different production stages. That is to say, flow intervention is required to obtain proper sampling. The inventors have estimated that the data will be obtained in a non-invasive and non-destructive way, and that these data is obtained independently of the mixing state of the flowing fluids, which will provide important costs reductions benefits, as well as a reduction in the time needed to carry out the measurements. To this end, the inventors have established that Nuclear Magnetic Resonance turns out to be a non-invasive and non-destructive technique that can be used to obtain a flow meter and a fraction meter, thus enabling a device and procedure to simultaneously measure both the flow and the fraction of the fluids flowing through a pipe. The inventors know that when magnetic moments, such as the nuclear spins of hydrogen atoms, are introduced in an external magnetic field, they have a tendency to align along the magnetic field giving rise to nuclear magnetization, which spins from a precession about this magnetic field at a characteristic frequency known as the resonance frequency.

In this way, and as a consequence of the presence of the external magnetic field, the nuclear spins reach a new equilibrium state. The time required to reach this new equilibrium state, measured from the instant in which the nuclear system is introduced in the magnetic field, is known as the "Spin-Lattice Relaxation Time", and is indicated as $T_1$. $T_1$ values depend on the many physical phenomena undergone by the spin system. Among these are the temperature, the system dynamics, the molecular structure in which the hydrogen atom exists, the molecular dynamics, the intramolecular and intermolecular interactions, and others. If the nuclear magnetization departs from its equilibrium state, its component perpendicular to the externally applied magnetic field decays away in a characteristic time known as "Spin-Spin Relaxation Time", which is indicated as $T_2$. $T_2$ values depend also on many physical phenomena undergone by the spin system, among which include the temperature, the molecular structure, the molecular dynamics, and others, with these being perhaps those that are the most important. Particularly, in an heterogeneous system, such as in an oil and water fluid mixture, the hydrogen nuclei in the oil and molecules in the water are well differentiated by means of their spin-lattice and spin-spin relaxation times due to the various and different processes and physical phenomena undergone by the two types of molecules. Additionally, other relaxation processes may be accounted for. One of the most relevant ones is the so called "Rotating System Spin-Lattice Relaxation Time", which is indicated as $T_{1\square}$. Nuclear Magnetic Resonance literature is replete with experimental techniques as to how to move the nuclear magnetization away from its state of equilibrium. Indeed, in this sense, it is known that many scientific works have been published previously to the innovations contained herein. For example, account has been given to the books "The Principles of Nuclear Magnetism" by A. Abragam (Clarendon Press, Oxford, 1961) and "Principles of Magnetic Resonance" by C. P. Slichter (Springer-Verlag, New York Heidelberg Berlin, 1990). In addition, account has been given to the published works of R. R. Enrst y W. A. Anderson in "The Review of Scientific Instrument", Vol. 37, N° 1, Page 93, 1966, and the work of R. Bageira de Vazconcelos Azeredo, A. L. Colnago y M. Engelsberg, namely "Analytical Chemistry", Vol. 72, N° 11, Page 2401, 2000. In order to have a flow meter to measure fluid flow and fluid fractions, and a procedure to record fluid flow and fluid fractions of a fluid flowing fluid in a duct, various techniques are available, one of which is a radio frequency pulse techniques. In this technique, a coil wound around the fluid to be measured and a series of pulses of alternating current applied to the fluid at the resonant frequency or at a frequency that is slightly shifted in order to move the nuclear magnetization away from its equilibrium state or position. Once the pulse ends, the magnetization returns to its equilibrium position, but does so in precession about the externally applied magnetic field. This precession induces an alternating voltage in the coil, which is referred to as the Nuclear Magnetic Resonance signal, whose amplitude is proportional to the number of hydrogen nuclei present in the fluid sample and whose temporal evolution depends on both spin-lattice and spin-spin relaxation processes. The information contained in the Nuclear Magnetic Resonance can be used to determine the fluid flow as well as the fraction of each of its components independently if these components are emulsified or phase separated.

DESCRIPTION OF THE DRAWINGS

The enclosed drawings are illustrative of the present invention. It is to be understood that the drawings are for illustration purposes only, and are not be construed as limiting in any way. In the drawings.

REFERENCES

In the above-described figures the same reference characters indicate same or complementary parts. In the drawings:

Reference Number 1 is reserved to indicate a computer;
Reference Number 2 is reserved to indicate a communication interface;
Reference Number 3 is reserved to indicate a board;
Reference Number 4 is reserved to indicate a radio frequency synthesizer;
Reference Number 5 is reserved to indicate a pulse programmer;
Reference Number 6 is reserved to indicate a receiver;
Reference Number 7 is reserved to indicate a low-noise preamplifier;
Reference Number 8 is reserved to indicate a mixer;
Reference Number 9 is reserved to indicate a video amplifier;
Reference Number 10 is reserved to indicate a transmitter;
Reference Number 11 is reserved to indicate a radio frequency switch;
Reference Number 12 is reserved to indicate a power preamplifier;
Reference Number 13 is reserved to indicate an attenuator;
Reference Number 14 is reserved to indicate a power amplifier;
Reference Number 15 is reserved to indicate a multiplexer;
Reference Number 16 is reserved to indicate a magnet;
Reference Number 17 is reserved to indicate a pole piece;
Reference Number 18 is reserved to indicate a yoke;
Reference Number 19 is reserved to indicate a duct;
Reference Number 20 is reserved to indicate a central section;
Reference Number 21 is reserved to indicate a first coil;
Reference Number 22 is reserved to indicate a second coil;
Reference Number 23 is reserved to indicate a pipe;
Reference Letter "a" is reserved to indicate a data center;
Reference Letter "b" is reserved to indicate a radio frequency unit;
Reference Letter "c" is reserved to indicate a Nuclear Magnetic Resonance;
Reference Letter "d" is reserved to indicate a circuit;
Reference Letter "h" is reserved to establish amplitude; and,
Reference Letter "$\tau$" or "T" is reserved to make reference to time. Reference characters h, $\tau$ and T mentioned above are sub-indexed, meaning they provide a reference to a given parameter.

SUMMARY OF THE INVENTION

In essence, the present invention features a various methods for determining the flow of fluids and the fraction of flowing fluids. The present invention also features the necessary equipment to carry out the methods, such as the flow meter, wherein the flow meter utilizes data handling central, a radio frequency unit, and a Nuclear Magnetic Resonance.

The method for determining fluid flow and fluid fractions comprises (a) determining the spin lattice relaxation time to be measured; (b) assigning radio frequency pulse sequences corresponding to each of the fluids to be measured and to the fluid flow; (c) applying a radio frequency pulse sequence to a first coil; (d) applying a second radio frequency pulse sequence to the first coil; and applying a third radio frequency pulse sequence to a second coil.

It is an object of some of the exemplary embodiments to provide a flow meter composed by a central data handling unit, a radio frequency unit, and a nuclear magnetic resonance unit.

DETAILED DESCRIPTION OF THE PREFERRED EMBODIMENT

The present invention is introduced by means of a purely demonstrative example, which in no means is intended to limit the invention. The components of the present invention could be chosen from various equivalents without altering the principles established in the present invention.

The components of the present invention featured in the various methods employed to determine the flow of fluids and the fraction of flowing fluids, as well as the components featured in the flow meter, are established in terms of their relationships and the results they are able to produce. With the end purpose of obtaining a fluid flow meter capable of measuring fluid flow passing through a pipe, as well as the fraction of each one of the components fluids, and to provide the ability of such a flow meter to perform similar measurements at various pre-established locations, it follows that such measurements are best obtain from the Nuclear Magnetic Resonance signal of the hydrogen nuclei contained in each of the fluid components.

Knowing that various fluids are differentiated by their corresponding spin-lattice relaxation times, a previous determination is required to be made of the relaxation times for each of the fluids to be measured.

Figure 1:
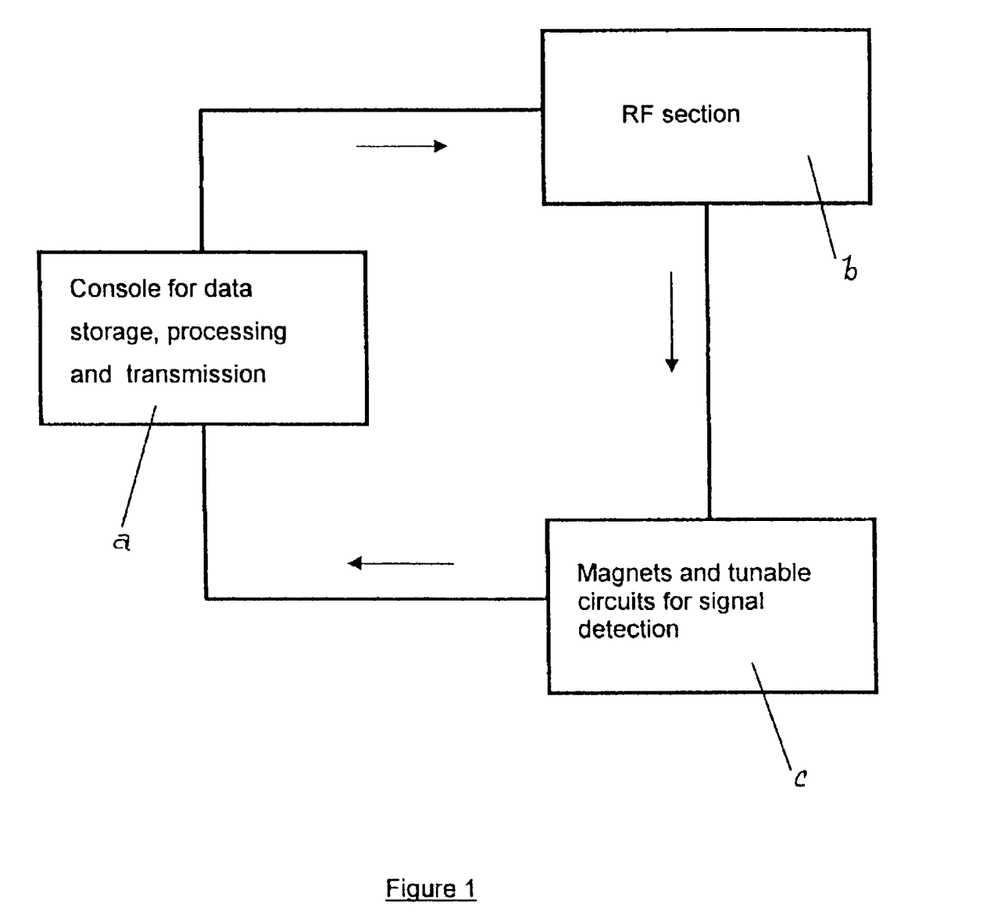
FIG. 1 shows a block diagram of the main components of the fluid flow and fraction meter.

The present flow meter as illustrated in FIG. 1, is made up of three principal elements or blocks. The first block is the data handling and processing central "a" consisting of a computer 1 with the specifications needed to carry out the required data processing, and with enough capacity to store the required information. This second block is the radio frequency unit "b" that is integrated with elements that allow amplification of the radio frequency pulses to be used to perturb the nuclear magnetization. The third main block is the Nuclear Magnetic Resonance unit "c."

Figure 2:
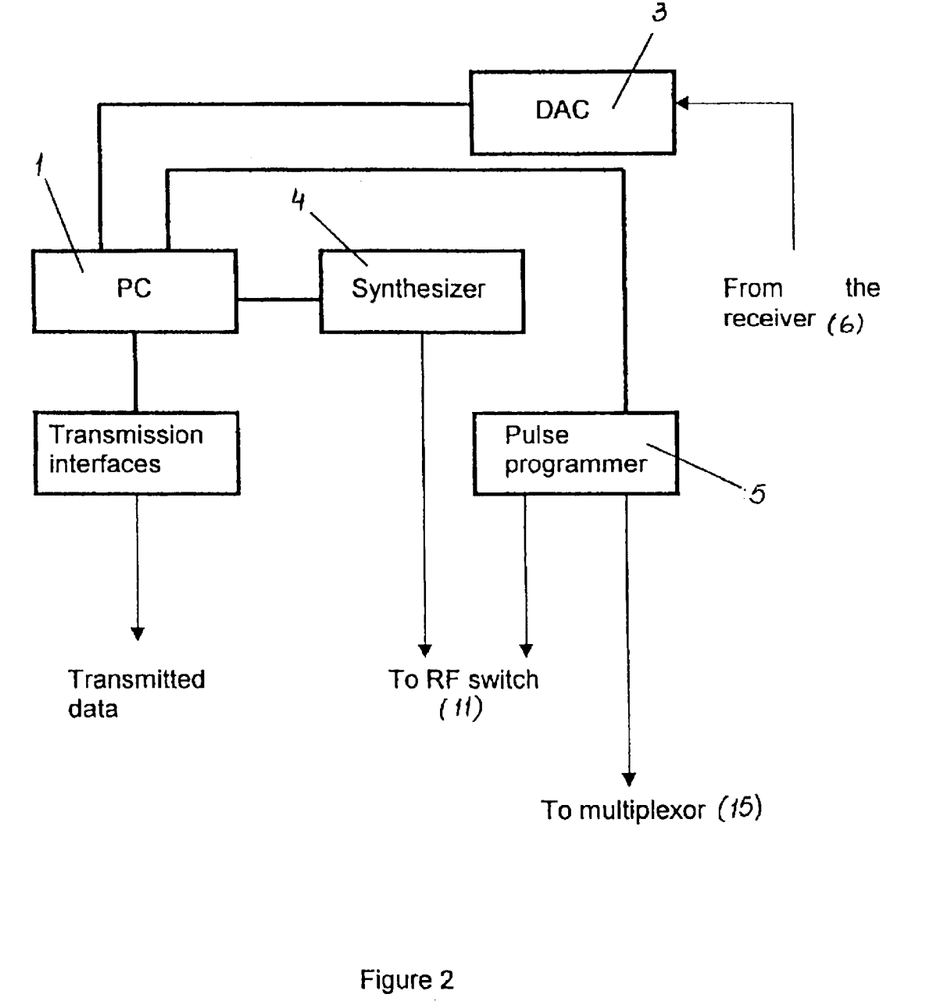
FIG. 2 exhibits a block diagram of the data central processing unit.

Referring to FIG. 2, computer 1 is loaded with the necessary measurement software and is linked by means of a communication interface 2 that allows bi-directional flow of information to distant places; a data acquisition and digitalization board 3; a frequency synthesizer 4 used to produce the radio frequency pulses, and a pulse programmer 5 that allows control of the radio frequency pulses, as well as the data acquisition and the multiplexing switch.

Figure 3:
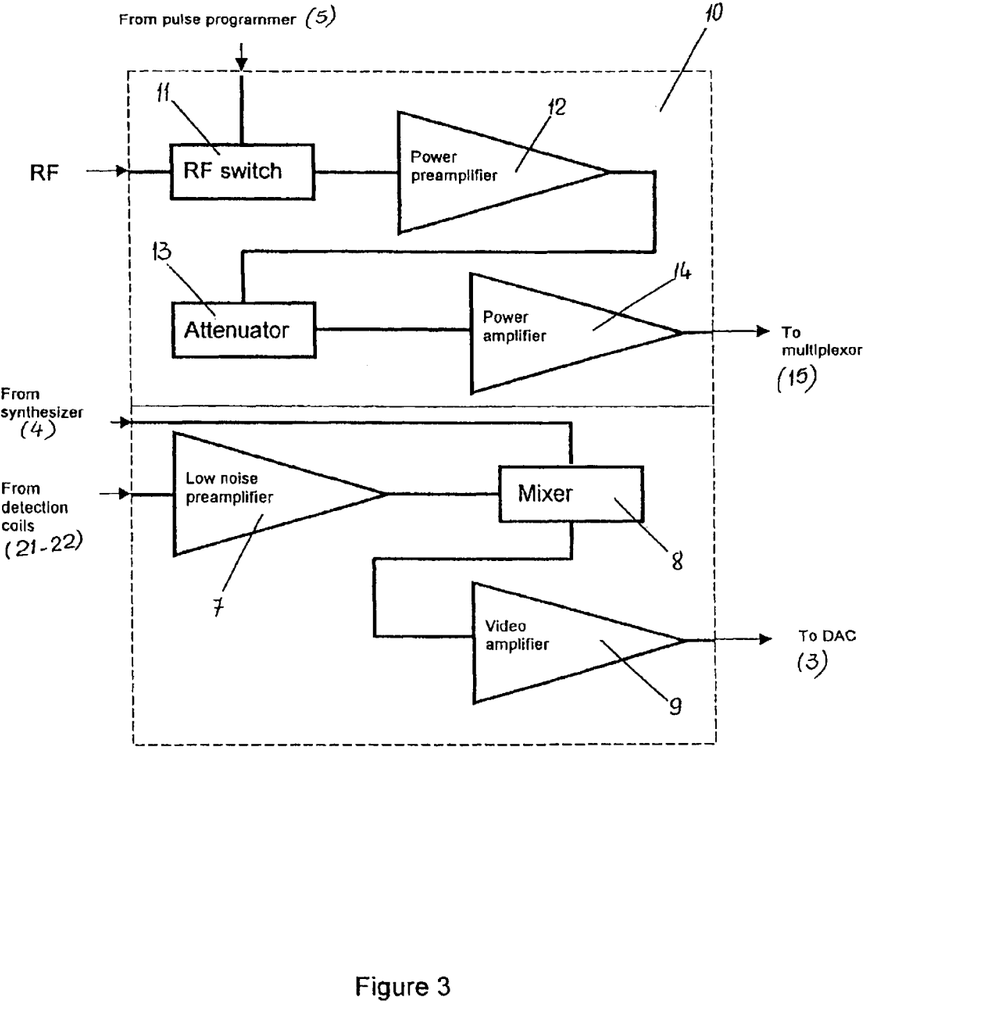
FIG. 3 a block diagram of the main components of the radio frequency unit.

With reference to FIG. 3, the second block is radio frequency unit "b" which is integrated with elements that allow amplification of the radio frequency pulses to be used to perturb the nuclear magnetization. Thus, radio frequency unit b consist of a receiver 6 integrated with a low-noise preamplifier 7 that is linked to a mixer 8, which is in turn linked to the radio frequency synthesizer 4 and a video amplifier 9, which feeds the information to the board 3. The function of the receiver 6 is to amplify the nuclear magnetic resonance signal to allow for this signal's acquisition and analog to digital conversion by digitalization board 3, which subsequently sends the signal to computer 1 for processing and, if required, for transmission by means of the communication interface 2. Radio frequency unit "b" further comprises a transmitter 10 integrated with a radio frequency switch 11 linked to a power preamplifier 12 that feeds an attenuator 13. Attenuator 13, in turn, links to a power amplifier 14 that is also linked to multiplexer 15, which derives from receiver 6.

Figure 4:
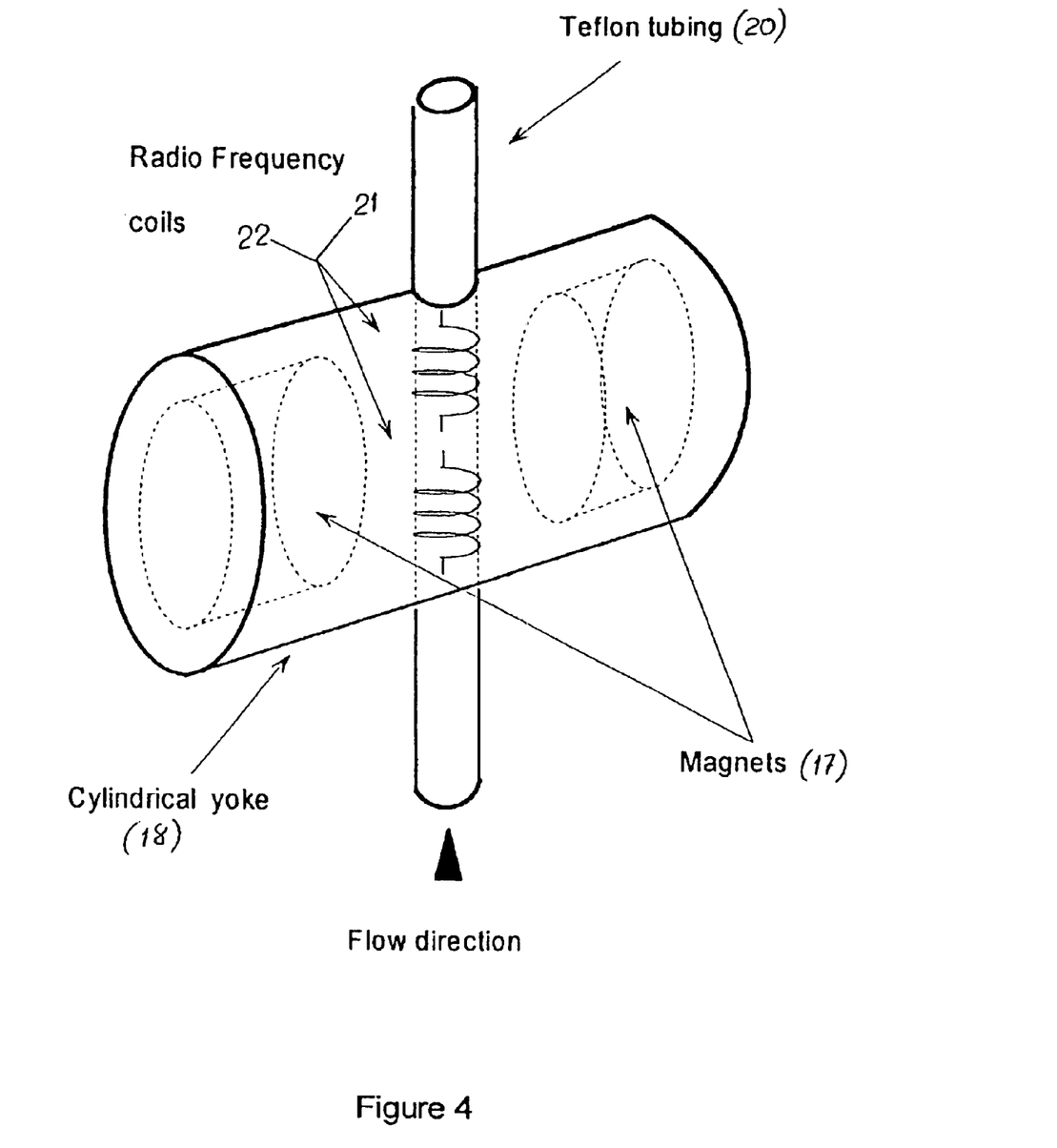
FIG. 4 shows the schematics of the general magnet diagram.
Figure 5:
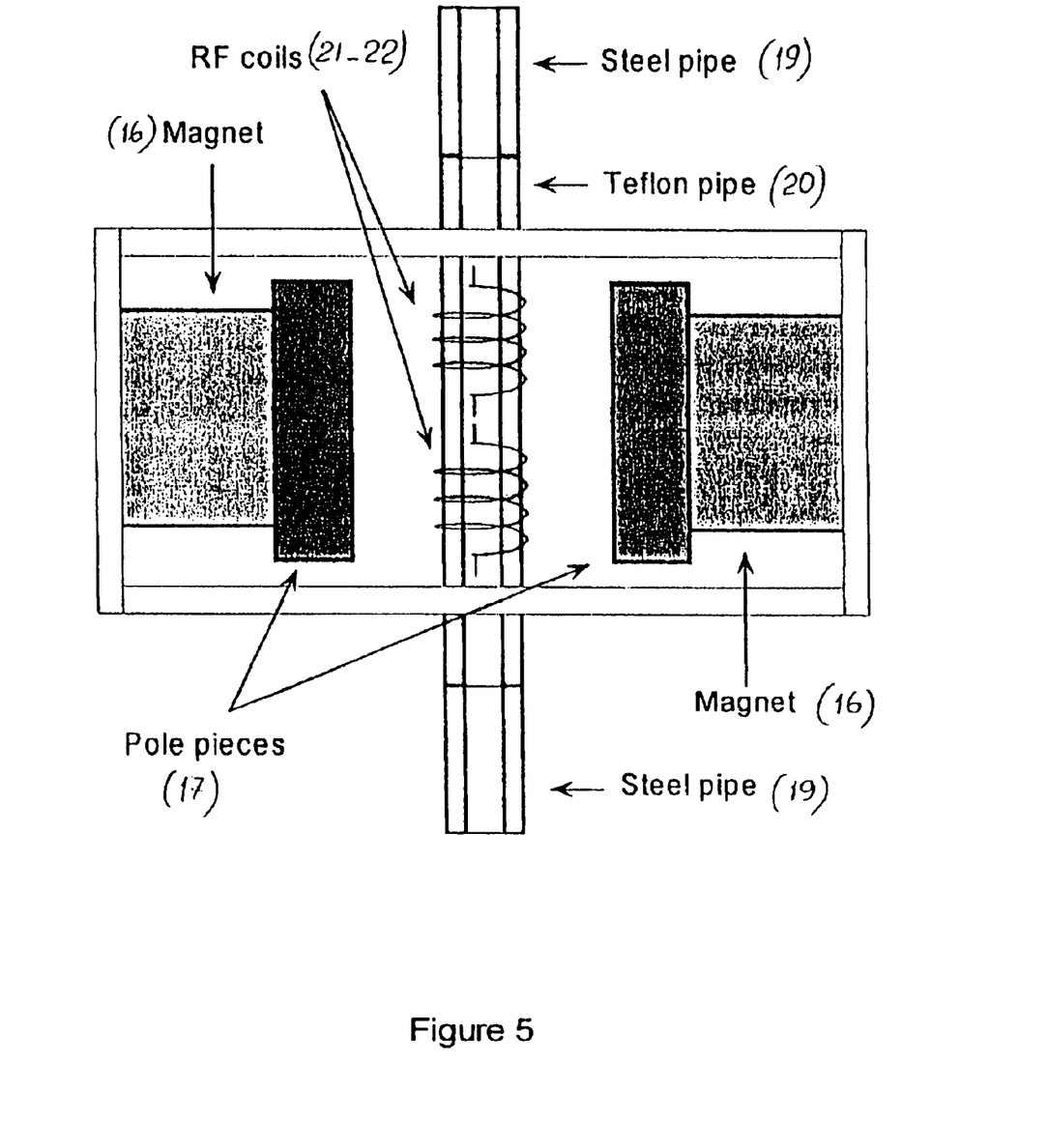
FIG. 5 shows a transverse view of the magnet.

The purpose of the transmitter 10 is to amplify the radio frequency pulses to be sent to Nuclear Magnetic Resonance unit "c." This nuclear magnetic resonance unit "c" has a magnet, which provides an stable external magnetic field to polarize the nuclear magnetic moments. As illustrated in FIGS. 4 and 5, the magnet is made up of two solid volume, cylindrically shaped, permanent magnetic material pieces 16, as well as to two cylindrically pole pieces 17 that function to increase the homogeneity of the produced magnetic field. Both, magnetic material 16 and the pole pieces 17 are mounted in a yoke 18, thus leaving room for a pipe 19 through which flows the fluid to be measured.

Figure 6:
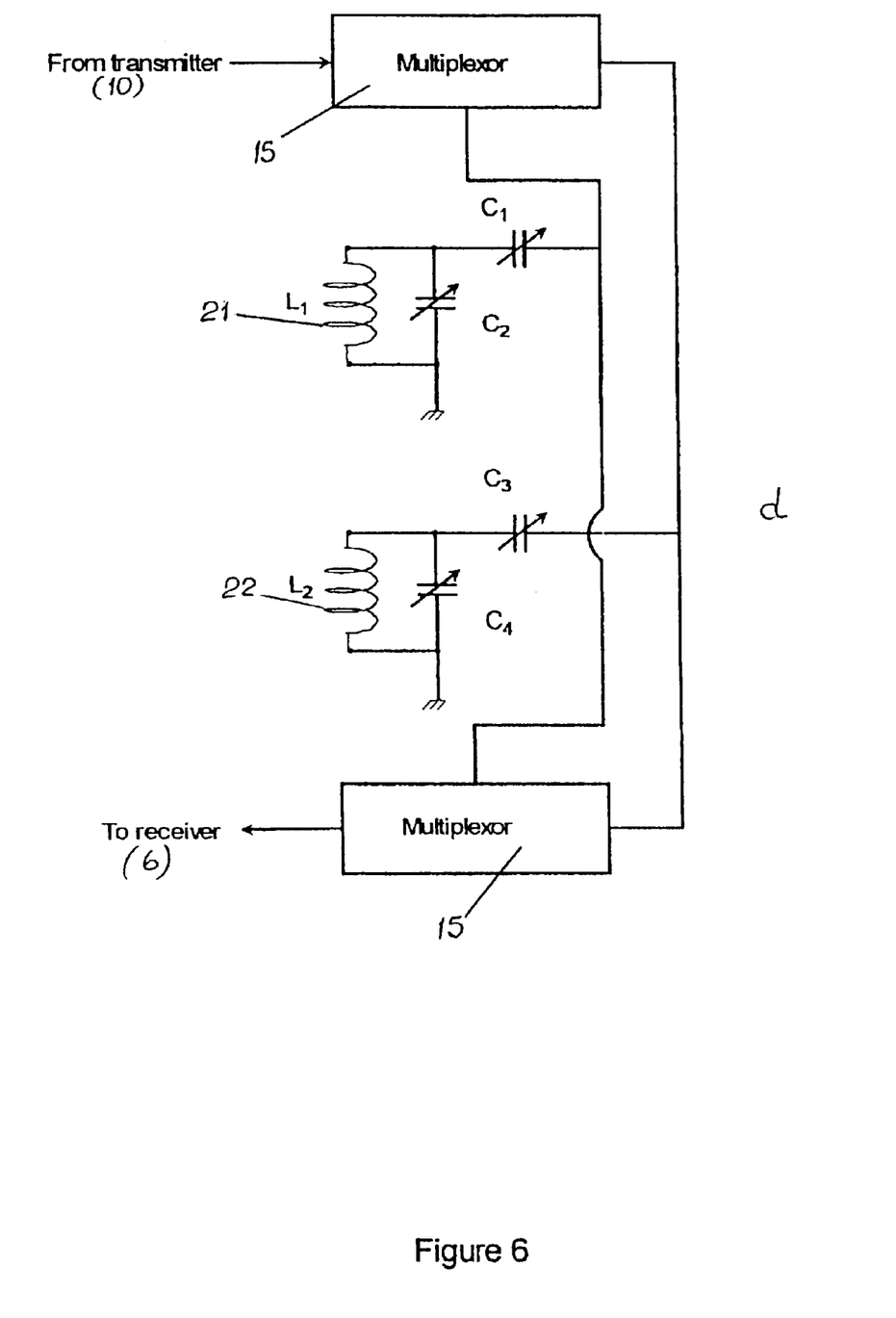
FIG. 6 exhibits a general diagram of the detection tuned circuitry.

Pipe 19 comprises a centralized part 20 made of synthetic type material, such as Teflon, arranged in between solid walled pieces that allow proper matching to any flow, or in other words, that insures the maintenance of a given and proportional flow through first coil 21 and through a second coil 22 in the detection circuitry "d." Detection circuitry "d" is made up of two identical coils, namely first coil 21 and second coil 22 deployed about central part 20 in such a way that, taking the flow direction of the fluid as a reference, one of them sits at beginning while the other sits at the end of the homogeneous zone of the magnetic field. Detection circuitry "d" includes impedance matching circuitry connected to the transmitter 10 and to the receiver 6 through a multiplexer driven by pulse programmer 5, which selects which one of the two coils, coils 21 or 22, is to receive the radio frequency pulses and which detects the Nuclear Magnetic Resonance signal.

Figure 7:
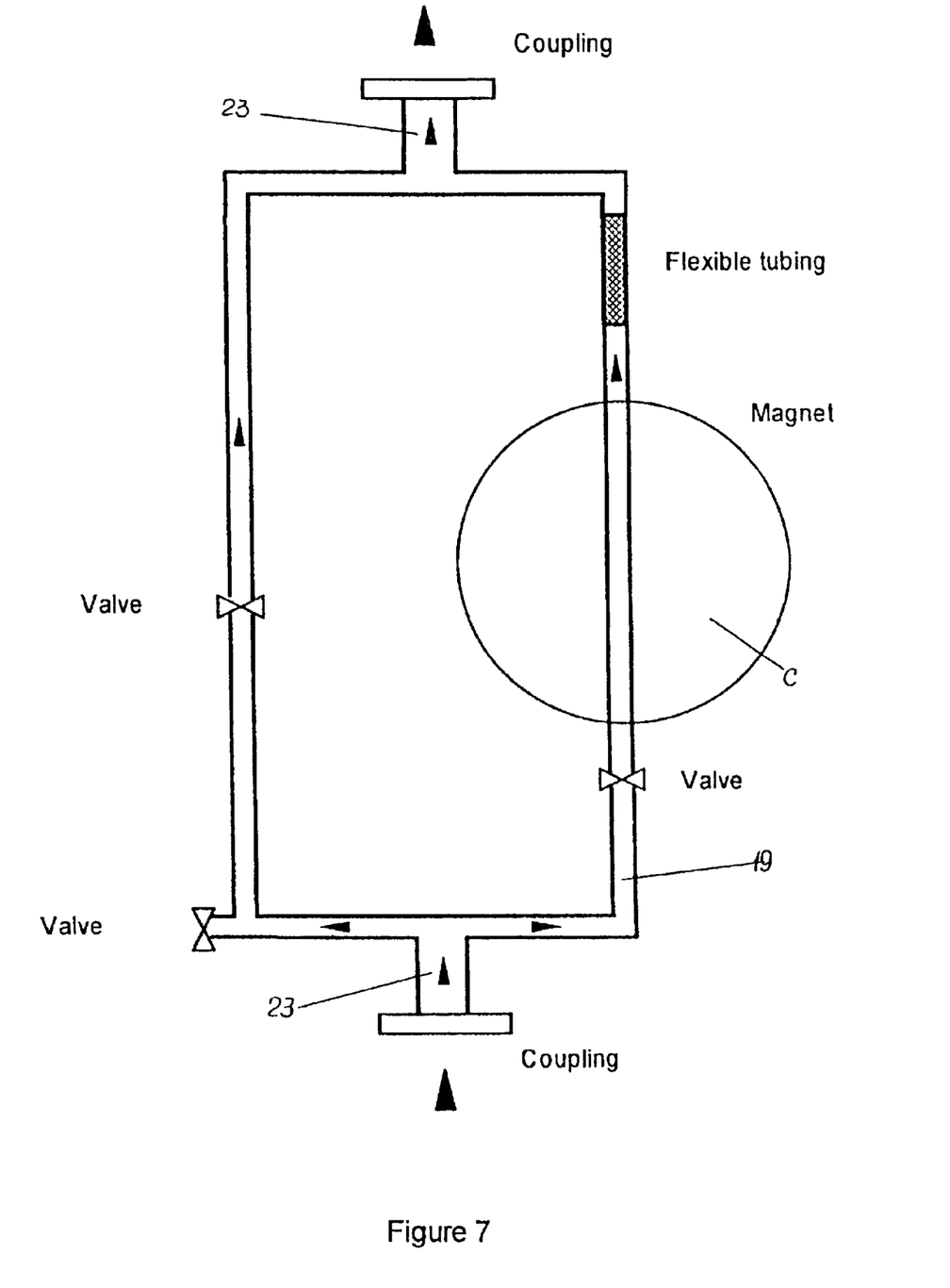
FIG. 7 shows the schematics of the magnet set up.
Figure 8:
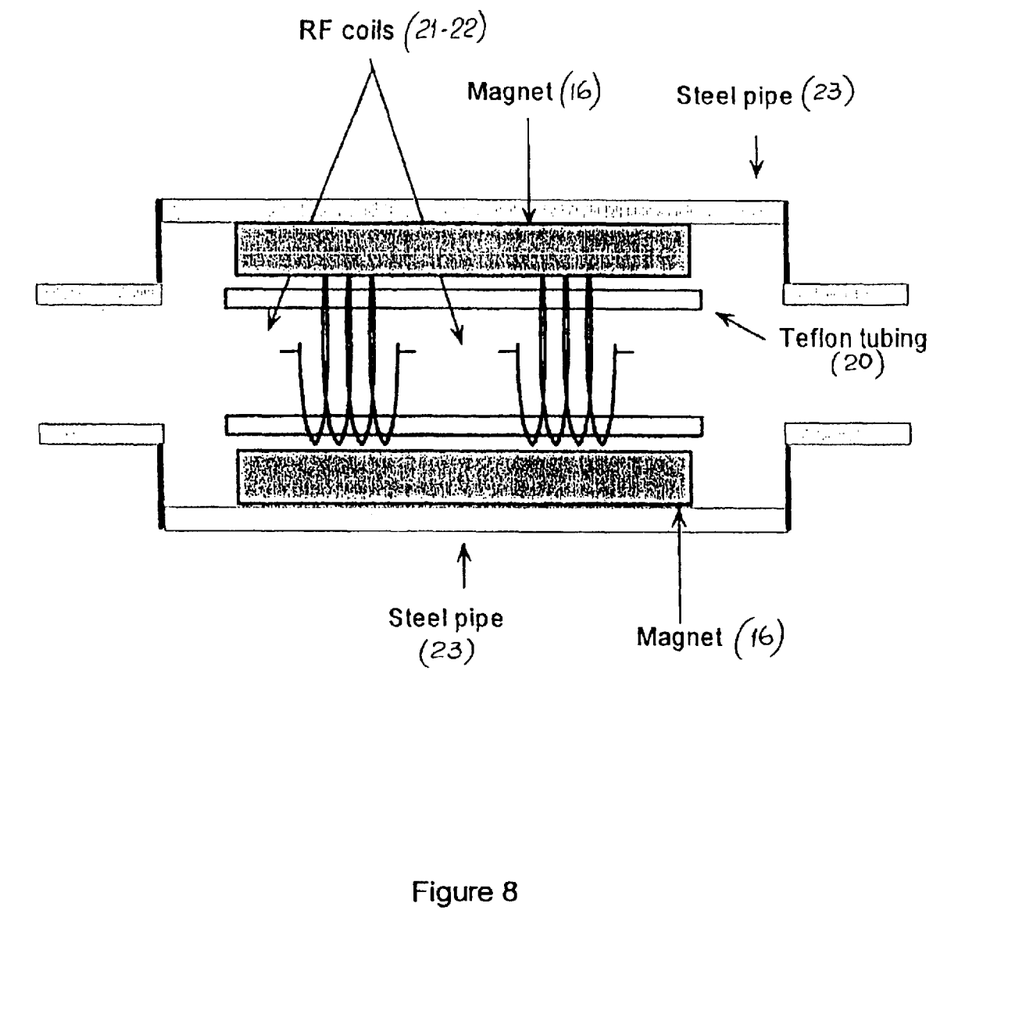
FIG. 8 shows the schematics of a possible realization of magnet set up for large section piping.

The radio frequency pulses derived to coils 21 or 22, according to the selection done by the pulse programmer 5 and according pre-established instructions programmed in the computer 1, produce a high frequency magnetic field that perturbs the nuclear magnetization. In an alternative realization, the Nuclear Magnetic Resonance unit "c" may be mounted at the interior of a pipe 23. This situation may be necessary in the oil industry if a large section production line is used, such as is schematically shown in FIG. 7 or 8.

The fluid flow and fluid fraction meter described herein may be realized in such a way that a magnet and the detection tuned circuitry are mounted on each pipe 23, thus sharing the same central data handling and processing unit "a," as well as the same radio frequency unit "b." In this realization, which is ideal for a crude oil collecting battery, the flow and fraction of oil and water measurements are carried on in an alternate and parallel way.

Figure 9:
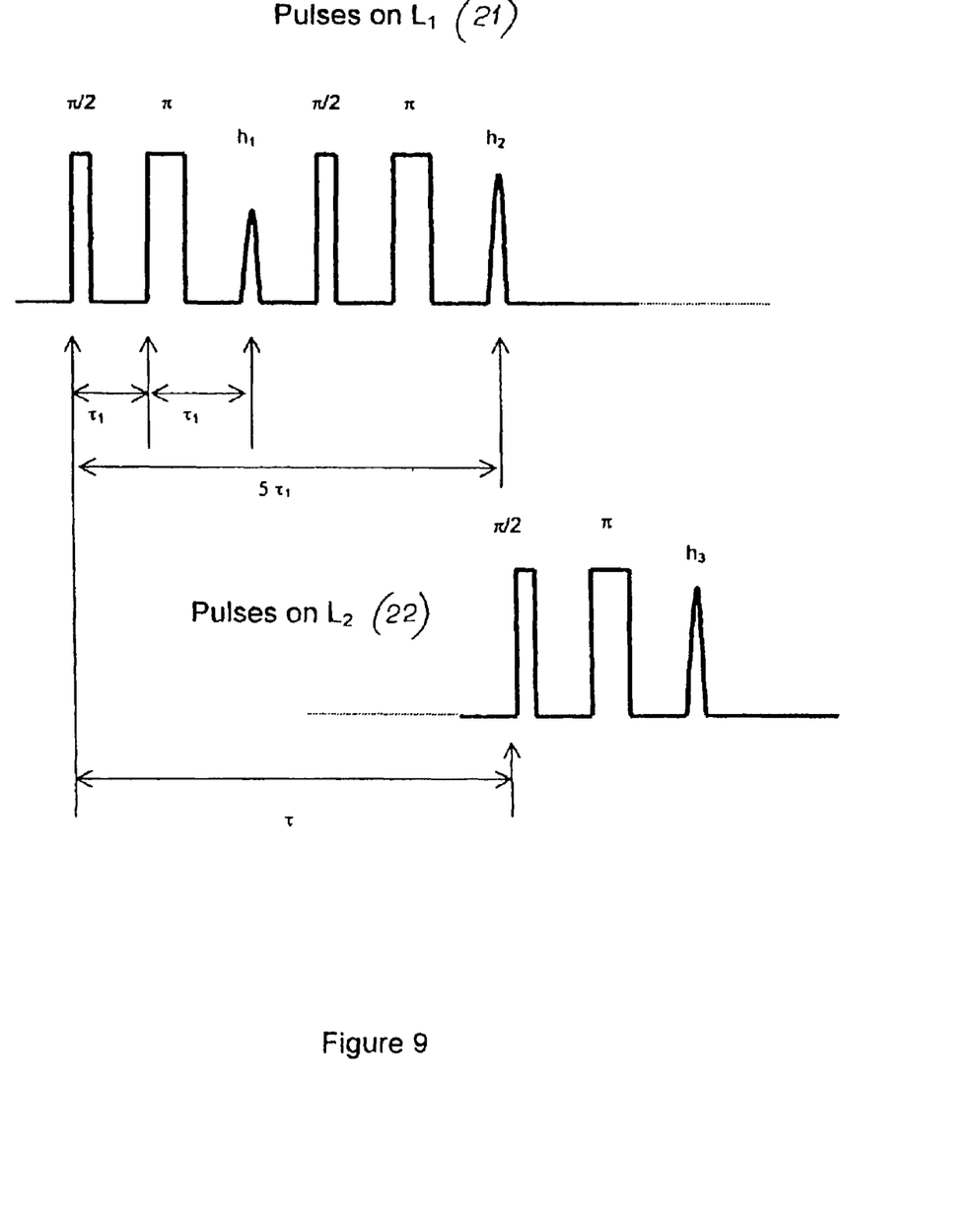
FIG. 9 shows the schematics of pulse sequences to measure spin-echo and steady-state free precession.
Figure 10:
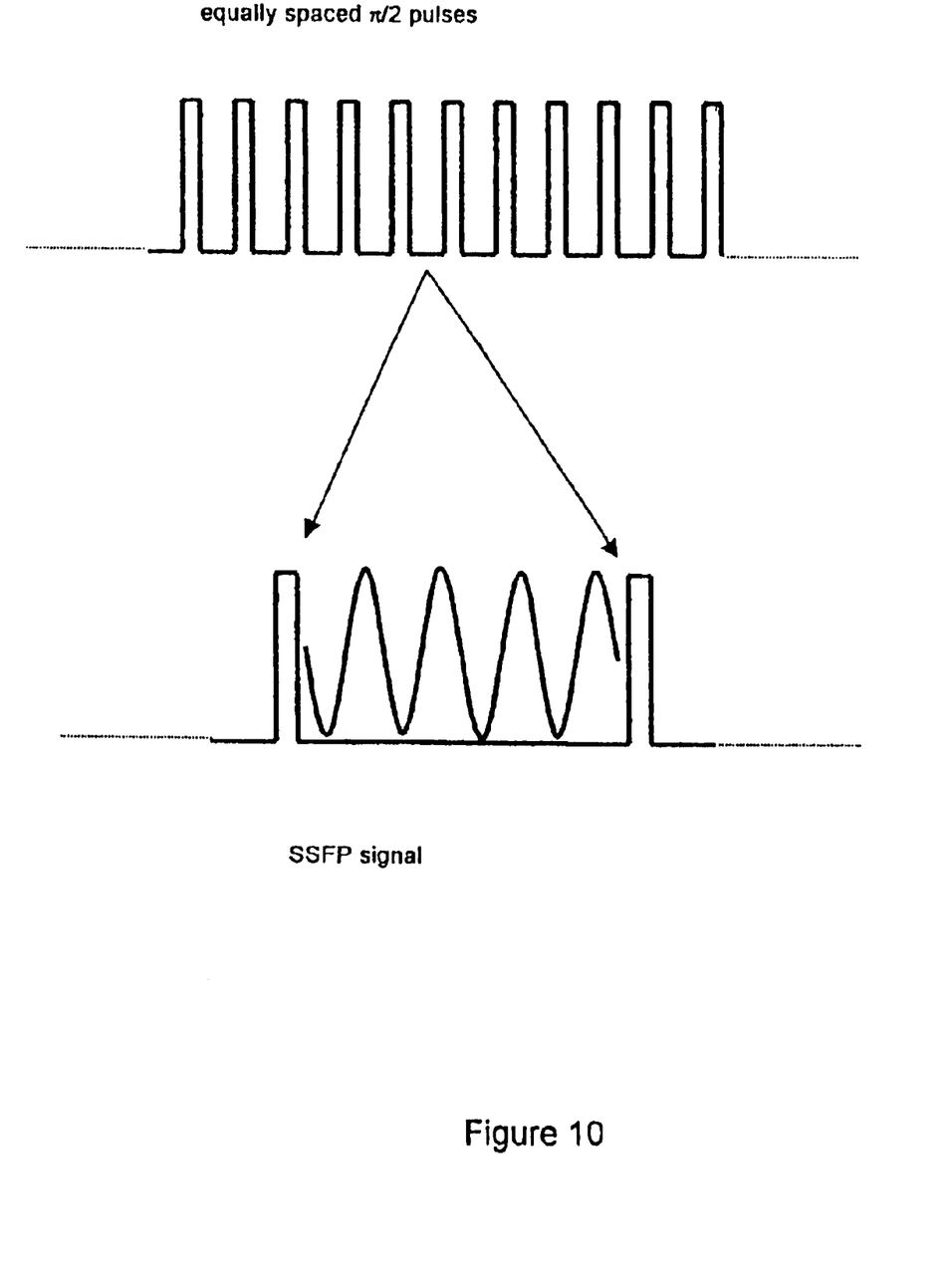
FIG. 10 shows the schematics of the steady-state free precession.

With the end purpose being to provide a method to determine fluid flow and fluid fraction, by means of the flow meter already described, a real case is provided as a concrete example. Within the extractive oil industry it is often necessary to determine the respective amounts of the total oil, water, and gas mixture flowing through a pipe. The first step in the method is to determine the spin-lattice of the identified fluids to be measured. The second step is to set up the radio frequency pulse sequences to be used in order to obtain measurements of the amounts of oil and water as well as the total flow in the circulating fluid. As such, the pulse sequences used are the spin echo, in the case of oil and water, and the steady state free precession in the case of total flow as is illustrated in FIGS 9 and 10.

The spin echo sequence is used in such a manner that, in a third step, a two radio frequency pulse train is applied to first coil 21. The first of these two pulses rotates the nuclear magnetization by 90°, therefore being called a $\pi/2$ pulse. The second pulse, in turn, has a length twice that of the first, therefore being called a $\pi$ pulse and being applied at a time $\tau_1$ that is short compared with the time $T_1$ of the formation water. This produces the nuclear magnetic resonance signal known as the spin-echo, or simply the echo, at exactly the same time $\tau_1$ after the second pulse. The echo amplitude $h_1$ is a nuclear magnetic resonance signal parameter that turns out to be directly proportional to the total number of hydrogen nuclei at the oil molecules, but only to a few ones of the hydrogen nuclei at the water molecules. This is due to the fact that the oil $T_1$ time is much shorter than the water $T_1$ time.

The fourth step, comprises applying a second radio frequency train pulse sequence similar to the previous one. Having obtained a second echo at $5\tau_1$ from the first applied pulse, its amplitude $h_2$ of this second radio frequency will be directly proportional to the amount of oil contained in the volume of the first coil 21. The contribution to the Nuclear Magnetic Resonance echo coming from the water molecules will have been completely attenuated.

Next, a time larger than that of the water $T_1$ is provided. Therefore, a fifth step comprises applying a third train pulse sequence to second coil 22 that is identical to the previous one, thus producing an echo whose amplitude $h_3$ is directly proportional to the full amount of oil and water contained in the volume of the mentioned second coil 22. Therefore, in an evaluation of the difference between the echo amplitude $h_3$ in the second coil 22 and the echo amplitude $h_2$ produced by the second pulse train, the total amount of water is obtained. In addition, by dividing the previously obtained result by the time, the flow speed of the circulating mixture of fluids is obtained.

In the alternative realization, represented in FIG. 10, the steady-state free precession pulse sequence may be used. In this embodiment, in the third step an equally spaced $\pi/2$ continuous train pulse sequence is applied during a fixed time $\tau$, therefore producing a nuclear magnetic resonance signal which is proportional to the flowing fluid speed and to the relaxation times.

This property allows to separate out oil from water by controlling the length of the pulses and by changing the separation time among them. Additionally, knowing that the oil $T_1$ time is much shorter than that of water, first coil 21 is used with a properly chosen steady state free precession sequence for oil detection and second coil 22 with a properly chosen one for water detection. The signal difference is compared with echo amplitudes obtained by coils 21 and 22 full of oil and water.

The above detailed description has presented a sequence of steps and a possible way to practice the invention, as well as the principles on which it is based. It will therefore be appreciated by those skilled in the art that yet other modification could be made to the present invention without deviating from its spirit and scope as so claimed.

What is claimed is:

1. A method for measuring and determining fluid flow and fluid fractions of a mixture of fluids comprising:

determining a spin-lattice relaxation time for a plurality of fluids to be measured;

assigning a radio frequency pulse sequence to each of said plurality of fluids, said radio frequency pulse sequence corresponding to each respective fluid and fluid flow to be measured, said frequency pulse sequences being used to identify a Spin Echo of said fluids to be measured and a steady-state free precession, each of which function to determine the flow of the fluids;

applying a radio frequency pulse sequence to a first coil;

applying a second radio frequency pulse sequence to said first coil; and applying a third radio frequency pulse sequence to a second coil.

2. The method of claim 1, wherein the frequency pulse sequences assigned comprise two pulses, with a first pulse functioning to rotate a nuclear magnetization by 90 degrees and a second pulse functioning to rotate the nuclear magnetization by 180 degrees, thus producing a signal of nuclear magnetic resonance at a time equal to the time between pulses after the second pulse, and having a signal amplitude as a parameter of the nuclear magnetic resonance signal that is directly proportional to the number of nuclei of a determined element of the molecules of a first fluid component and only directly proportional to a portion of the number of nuclei of a determined element of a second fluid component.

3. The method of claim 1, wherein the second radio frequency pulse sequence produces a second signal time shifted from the first radio frequency pulse sequence, wherein said second signal comprises an amplitude that is proportional to an amount of resonant spins of a first fluid to be measured that is contained in a volume of the first coil, and is completely attenuated in relation to the second fluid to be measured.

4. The method of claim 2, wherein the third radio frequency pulse sequence produces a signal having an amplitude directly proportional to the total number of nuclei in the fluids that are contained in the second coil, wherein the difference between the amplitude of the echo in the second coil and the echo of the second pulse sequence determines an amount of one of the fluids being measured.

5. The method of claim 1, wherein a continuous sequence of equally spaced pulses is applied during a fixed time in order to obtain a nuclear magnetic resonance signal having an amplitude that is directly proportional to a velocity of the fluid flow and to the spin-relaxation times, and wherein one of the coils provides a different sequence of steady-state free precession that is adequate for the detection of one of the fluids to be measured.

6. The method of claim 1, wherein each of said recited steps of applying are carried out by a fluid flow and fluid fraction meter comprising:

a data processing unit having a computer processor linked to a data acquisition and digitalization board;

a radio frequency unit having a pulse programmer that sends out radio frequency pulses that create a high frequency magnetic field used to perturb nuclear magnetization;

a nuclear magnetic resonance unit having one or more magnets and tunable circuits, said nuclear magnetic resonance unit receiving said radio frequency pulses to produce a nuclear magnetic resonance signal.

7. The method of claim 6, wherein said magnet and a detection tuned circuitry are each mounted to one or more pipes of a crude oil collector battery, thus sharing the same central unit and the same radio frequency and enabling the flow and fractions of said fluid to be measured in a parallel and alternating way.

8. The method of claim 6, wherein said radio frequency unit comprises a receiver integrated with a low-noise preamplifier linked to a mixer, which is in turn linked to radio frequency synthesizer and a video amplifier, which feeds the information to a digitalization board, said receiver functions to amplify said nuclear magnetic resonance signal to allow for its acquisition and its conversion from analog to digital by a digitalization board, which subsequently sends the signal to computer for processing and for transmission by means of communication interface.

9. The method of claim 8, wherein said radio frequency unit further comprises a transmitter integrated with a radio frequency switch linked to a power preamplifier that feeds an attenuator, which said attenuator, in turn, links to a power amplifier that is also linked to a multiplexer, which derives from receiver.

10. The method of claim 9, wherein said magnet of said nuclear magnetic resonance unit comprises a stable external magnetic field used to polarize one or more nuclear magnetic moments, said magnet is made up of two solid volume, cylindrically shaped, permanent magnetic material pieces and two cylindrical pole pieces that function to increase the homogeneity of said magnetic field.

11. The method of claim 10, wherein said magnetic material pieces and said pole pieces are mounted in a yoke, thus leaving room therein for a pipe through which flows said fluid.

12. The method of claim 11, wherein said pipe comprises a centralized part arranged between solid walled pieces that allow proper matching of any fluid flow and that ensures maintenance of a given and proportional flow through a detection circuitry, said detection circuitry made up of first and second coils deployed about said centralized part in such a way that, using the flow direction of said fluid as a reference, said coils are at opposite ends of a homogenous zone of said magnetic field.

13. The method of claim 12, wherein said detection circuitry comprises impedance matching circuitry connected to said transmitter and to said receiver through a multiplexer driven by a pulse programmer, which selects which one of said two first and second coils is to receive said radio frequency pulse and which one is to detect said magnetic resonance signal, said coil receiving said radio frequency functions to product said high frequency magnetic field.

14. The method of claim 12, wherein said magnet and said detection circuitry are mounted on a pipe and share said central data handling and processing unit.

15. The method of claim 6, wherein said nuclear magnetic resonance unit is mounted internally within a pipe.

* * * * *